US006602197B2

(12) United States Patent
Tahara

(10) Patent No.: US 6,602,197 B2
(45) Date of Patent: Aug. 5, 2003

(54) ULTRASONIC PROBE

(75) Inventor: Yoshihiro Tahara, Saitama (JP)

(73) Assignee: Nihon Dempa Kogyo Co., Ltd., Tokyo (JP)

( * ) Notice: Subject to any disclaimer, the term of this patent is extended or adjusted under 35 U.S.C. 154(b) by 0 days.

(21) Appl. No.: 10/131,125

(22) Filed: Apr. 25, 2002

(65) Prior Publication Data

US 2003/0018265 A1 Jan. 23, 2003

(30) Foreign Application Priority Data

Apr. 26, 2001 (JP) ....................................... 2001-128648

(51) Int. Cl.[7] ........................... A61B 8/00; H01L 41/22; H04B 11/00

(52) U.S. Cl. ........................ 600/459; 29/25.35; 73/1.82

(58) Field of Search ................................. 600/459, 472, 600/447, 466; 29/25.35; 73/1.82; 310/334–336, 358, 327; 53/131.2

(56) References Cited

U.S. PATENT DOCUMENTS 4,825,115 A * 4/1989 Kawabe et al. ............. 310/327
5,115,809 A * 5/1992 Saitoh et al. ............... 600/459
5,163,436 A * 11/1992 Saitoh et al. ............... 600/459
5,295,487 A * 3/1994 Saitoh et al. ............... 600/459
5,408,791 A * 4/1995 Marie ......................... 53/131.2
6,020,675 A * 2/2000 Yamashita et al. .......... 310/358

* cited by examiner

*Primary Examiner*—Marvin M. Lateef
*Assistant Examiner*—Ruby Jain
(74) *Attorney, Agent, or Firm*—Oblon, Spivak, McClelland, Maier & Neustadt, P.C.

(57) ABSTRACT

A variable type ultrasonic probe is provided, in which each of piezoelectric units accommodated in the probe is separated into a plurality of piezoelectric elements, and the piezoelectric units are easily arrayed in an arcuately curved arrangement. The ultrasonic probe has therein a piezoelectric unit separated into at least three piezoelectric elements, i.e., a central element and both opposite end elements, and disposed on a backing member in a manner such that a lower face electrode of each piezoelectric element is led out. A leading-out wiring board provided with conductive paths formed on both major faces thereof is arranged on the lower faces of the one end and central piezoelectric elements. The lower face electrodes of the one end element and central element are electrically led out by the upper face conductive path and the lower face conductive path of the leading-out wiring board, respectively.

10 Claims, 2 Drawing Sheets

ULTRASONIC PROBE

BACKGROUND OF THE INVENTION

1. Field of the Invention

The present invention relates to an ultrasonic probe, and more particularly to a variable type ultrasonic probe capable of changing over the focus from one to the other in a depth direction by separate arrangement of piezoelectric elements in a widthwise direction.

2. Description of the Related Art

An ultrasonic probe is used in, for example, ultrasonic diagnostic equipment for medical care purpose, as an ultrasonic transducer, which transmits and receives an ultrasonic wave, for acquiring information of a living organism from the disease portions. There are various kinds of ultrasonic probes depending on functions and shapes of the probes, and as one of them, there is an ultrasonic probe capable of changing over the focus thereof in a depth direction from the surface of a living body, i.e., a tested body. This type of an ultrasonic probe is called a variable type probe.

FIG. 1 illustrates the constitution of a conventional variable type probe in which a plurality of piezoelectric units 1 is arrayed in a line on backing member 2. Each piezoelectric unit 1 is provided with a piezoelectric member, and excitation electrodes provided on the upper and lower faces of the piezoelectric member, respectively. Further, piezoelectric unit 1 is separated into three pieces, namely, piezoelectric elements 1*a*, 1*b* and 1*c*, in the widthwise direction.

The variable type probe is manufactured by the method described hereinbelow:

For example, flexible printed boards 3*a*, 3*b*, and 3*c*, which are used for externally conducting the excitation electrodes, are attached to the center and opposite sides of the bottom face of a plate-like member of piezoelectric body, and then inpouring or filling of resin is performed so as to form backing member 2. Subsequently, cuttings reaching from the piezoelectric plate-like member to backing member 2 are applied so as to sever the piezoelectric plate member in a lengthwise direction to thereby obtain a plurality of separate piezoelectric units 1. Then, the piezoelectric plate-like member is severed in a widthwise direction, so that each piezoelectric unit 1 is separate into three piezoelectric elements 1*a*, 1*b* and 1*c*, i.e., one central and two side-arranged elements. The lower face electrodes of piezoelectric elements 1*a*, 1*b* and 1*c* are led by flexible printed board 3*a*, 3*b* and 3*c*, respectively. Although upper face electrodes of piezoelectric elements 1*a*, 1*b* and 1*c* are not shown in FIG. 1, these upper face electrodes of piezoelectric elements 1*a*, 1*b* and 1*c* are electrically connected to and grounded by common electrode (not shown) which is arranged to cover the plurality of piezoelectric units 1.

In the described variable type ultrasonic probe, either three piezoelectric elements 1*a*, 1*b* and 1*c* separated widthwise are commonly driven or only the central piezoelectric element 1*b* is driven to thereby change over the focus from the surface of a living body from one to the other focal point. When the three piezoelectric elements 1*a*, 1*b* and 1*c* are simultaneously driven, the focal distance becomes long. On the other hand, when only the central piezoelectric element 1*b* is driven, the focal distance becomes short.

At this stage, in the ultrasonic probe, there are different types such as, for example, a convex type probe and a linear type probe, depending on how a plurality of piezoelectric elements are arranged in respective probes. In the convex type probe, as shown in FIG. 2, a plurality of piezoelectric elements 1 are arrayed to be directed outward along an arcuate line, and is therefore suitable for arcuately emitting ultrasonic wave so as to detect ultrasonic echo within a predetermined angular range. On the other hand, in the linear type probe, a plurality of piezoelectric elements 1 is arrayed in a straight line to be oriented in the same direction. The linear type probe is used for emitting ultrasonic wave in only a specified direction.

Backing member 2 of the variable probe shown in FIG. 1 has an approximately planar face without any curve, and piezoelectric units 1 are arrayed on such backing member 2. Thus, the variable type probe of FIG. 1 can be classified in the linear type probe.

In the variable type probe of FIG. 1, flexible printed board 3*b* is connected to central piezoelectric element 1*b*, which is one of three piezoelectric elements 1*a*, 1*b*, and 1*c* constituting piezoelectric element 1, so as to depend vertically as shown in FIG. 1 to thereby permit the lower face electrode to be led. Therefore, when the surface of backing member 2 is arcuately curved as shown in FIG. 2 while permitting a plurality of piezoelectric units 1 are arrayed thereon, flexible printed board 3*b* depending from the central piezoelectric elements 1*b* of respective piezoelectric units 1 might mutually interfere. Accordingly, in the variable type probe as shown in FIG. 1, it is difficult to constitute a convex type probe by arraying piezoelectric units 1 on a surface arcuately curved in a lengthwise direction, i.e., in a direction of array.

SUMMARY OF THE INVENTION

Therefore, an object of the present invention is to provide a variable type probe, which is easy to curvedly arrange a plurality of piezoelectric units on a curved face.

The above object of the present invention can be achieved by an ultrasonic probe including a backing member, a piezoelectric unit which is arranged on the backing member and constituted by at least three piezoelectric elements separated into one end portion, a central portion, and the other end portion, each of the piezoelectric elements having a lower face electrode thereof led out, wherein the ultrasonic probe comprises a leading-out wiring board having, on both major faces thereof, electrically conducting paths, and wherein the lower face electrode of the piezoelectric element of the one end portion being electrically led out by an upper one of the major faces of the leading-out wiring board, and the lower face electrode of the piezoelectric element of the central portion being electrically led out by a lower one of the major faces of the leading-out wiring board.

In the present invention, the leading-out wiring board having electrically conductive paths on both major faces is used, so that a lower face electrode of the piezoelectric element of the one end portion is electrically led by the upper face electric conductive path of the leading-out wiring board, and so that a lower face electrode of the piezoelectric element of the central portion is electrically led by the lower face electric conductive path of the leading-out wiring board. Therefore, the lower face electrode of the piezoelectric element of the central portion can be electrically led in a horizontal direction. Thus, according to adoption of this arrangement of the present invention, even when the surface of the backing member is arcuately curved, mutual interference among the leading-out wiring boards would not occur, so that, for example, a variable type probe formed in the convex type can be easily provided.

DETAILED DESCRIPTION OF THE INVENTION

Figure 1:
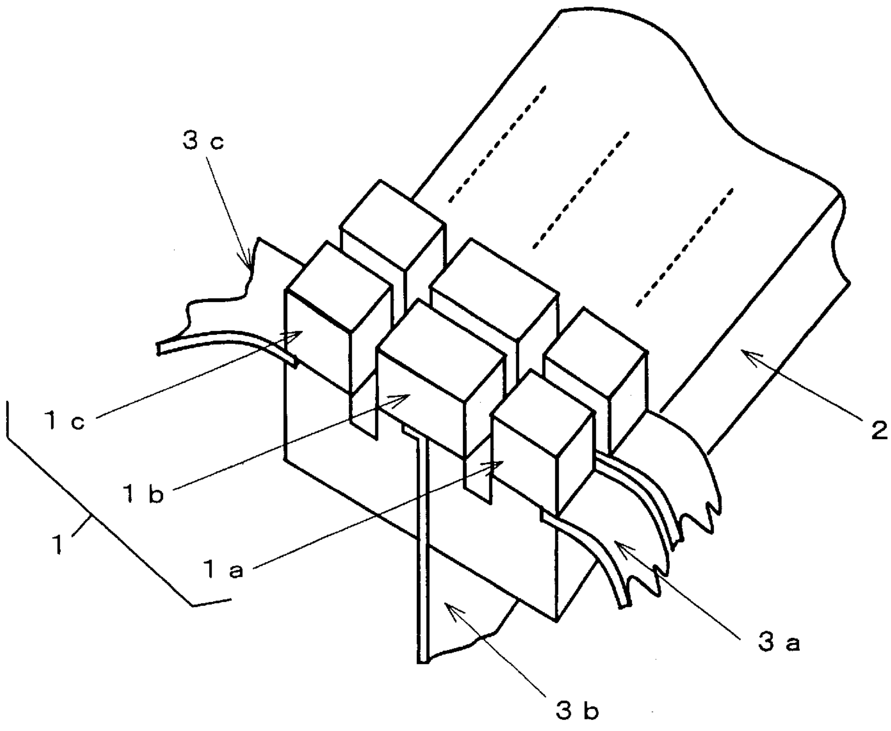
FIG. 1 (PRIOR ART)
FIG. 1 is a perspective view illustrating the conventional variable type ultrasonic probe.
Figure 2:
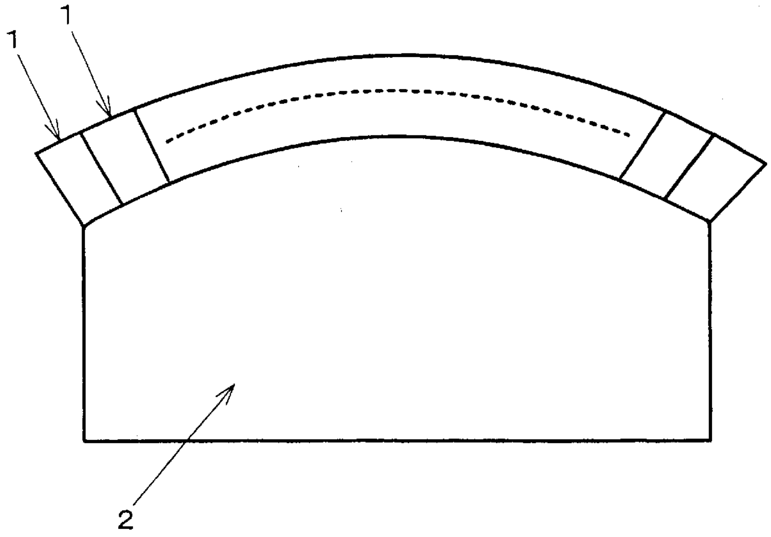
FIG. 2 (PRIOR ART)
FIG. 2 is a front view illustrating the conventional convex type ultrasonic probe.
Figure 3:
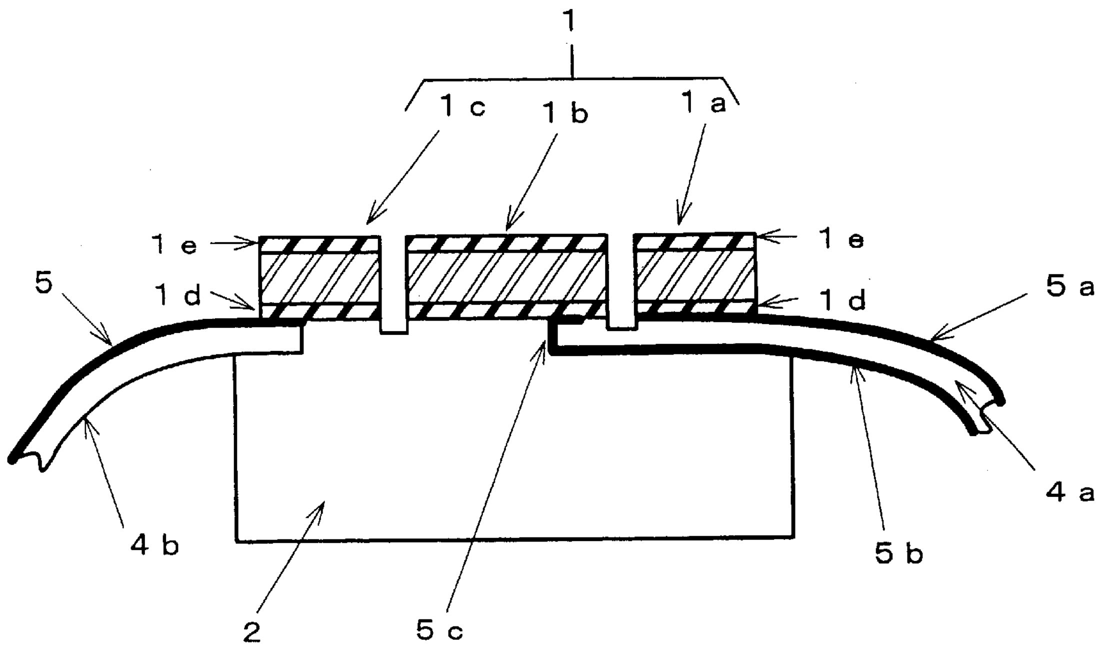
FIG. 3 is a side view illustrating a variable type ultrasonic probe according to an embodiment of the present invention.

In FIG. 3 illustrating a variable type probe according to an embodiment of the present invention, constituents of the unit designated by reference numerals the same as those of FIG. 1 are the same or like constituents, and accordingly description thereof in detail will not be repeated hereinbelow.

The variable type ultrasonic probe shown in FIG. 3 has, as described before, such a constitution that a plurality of piezoelectric units 1, each being constituted by piezoelectric elements 1*a*, 1*b*, and 1*c*, are arranged on backing member 2. The plurality of piezoelectric units 1 is arrayed in a direction vertical to the surface of the drawing sheet of FIG. 3. Further, lower face electrodes 1*d* of respective piezoelectric elements 1*a*, 1*b*, and 1*c* are electrically led out by two pieces of flexible printed boards 4*a* and 4*b*. One of flexible printed boards 4*a* and 4*b*, i.e., the flexible printed board 4*a* is formed in a multi-layer construction to have electric conductive paths 5*a* and 5*b* or patterns on both major faces thereof. Electric conductive path 5*b* on the rear face of multi-layer flexible printed board 4*a* is extended toward the front face side via through-hole 5*c* at the tip end of flexible printed board 4*a*. The other flexible printed board 4*b* is formed in a single-layer construction similar to the prior art construction and has electric conductive path 5 on only the upper face of flexible printed board 4*b*.

Now, a description of the manufacturing method of this variable type probe will be provided hereinbelow.

First, a multi-layer flexible printed board 4*a* is connected, by conductive adhesive or by soldering, to one side of a lower face of a piezoelectric plate provided with lower face electrode id and upper face electrode le formed on the respective major faces thereof, and a single-layer flexible printed board 4*b* is also connected, by conductive adhesive or by soldering, to the other side of the piezoelectric plate. At this stage, compared with the manufacturing of the conventional variable type probe, the multiple-layer flexible printed board 4*a* is attached to the piezoelectric plate in a manner such that it comes close to the central portion of the latter piezoelectric plate. Specifically, flexible printed board 4*a* is extended to a position confronting the central piezoelectric element 1*b*, and at that position, flexible printed board 4*a* is also connected to lower face electrode 1*d* of the piezoelectric plate.

Subsequently, the piezoelectric plate to which flexible printed boards 4*a* and 4*b* are connected in the described manner is fixedly secured onto backing member 2 in a manner similar to the prior art. Then, cuttings reaching from the surface of the piezoelectric plate to backing member 2 are provide for severing the piezoelectric plate in a lengthwise direction, in order to separate it into a plurality of separate piezoelectric units 1. Thereafter, each piezoelectric unit 1 is separated into three pieces by the application of cuttings in a widthwise direction from the upper face of the piezoelectric plate to thereby produce three piezoelectric elements 1*a*, 1*b* and 1*c*. At this stage, on one side of respective piezoelectric units 1, cuttings are carried out so as to sever respective piezoelectric unit 1 until apertures reaching multi-layer flexible printed board 4*a* are provided. During this cutting operation, electric conductive path 5*a* on the front side of flexible printed board 4*a* may be cut, but electric conductive path 5*b* on the rear side should be prevented from being cut. On the other side of respective piezoelectric units 1, cutting are carried out until cutting apertures reach backing member 2, to thereby sever respective piezoelectric units 1. Then, a common electrode to which each upper face electrode le is connected in common is provided by a method well known in the art.

According to the described constitution, lower face electrode id of piezoelectric elements 1*a* and 1*b* of one side portion and the central portion of respective piezoelectric units 1 are electrically led outside by electric conductive paths 5*a* and 5*b* on upper and lower faces of multi-layer flexible printed board 4*a*. Further, flexible printed boards 4*a* and 4*b* are led out of respective piezoelectric units 1 in horizontal directions, respectively. Therefore, even if each of piezoelectric units 1 are curvedly arranged in a direction of array, any mutual interference among the flexible printed boards which lead out of a plurality of piezoelectric units 1 would not occur, and accordingly it is possible to easily acquire a convex type ultrasonic probe.

In the embodiment of the foregoing description, although multi-layer flexible printed boards 4*a* are arranged on only one side of piezoelectric units 1, and although each of piezoelectric units 1 is cut and separated into three pieces, multi-layer flexible printed boards 4*a* may be arranged on, for example, both sides of the piezoelectric units and the each piezoelectric unit may be separated into four pieces. Also, the number of layers of flexible printed board 4*a* might be increased from two to three or more layers, so as to comply with a case where the respective piezoelectric units are separated into five or more pieces. Further, although the wiring board for the leading of the electrode is constituted by a flexible printed board, for example, a mere printed circuit board formed by providing electric conductive paths on a resin-made board may be used for constituting the wiring board for leading of the electrode.

What is claimed is:

1. An ultrasonic probe including a backing member, a piezoelectric unit which is arranged on the backing member and constituted by at least three piezoelectric elements separated into one end portion, a central portion, and the other end portion, each of said piezoelectric elements having a lower face electrode thereof led out, said ultrasonic probe comprising:
   - a leading-out wiring board having, on both major faces thereof, electrically conducting paths,
   - wherein the lower face electrode of said piezoelectric element of said one end portion being electrically led out by an upper one of said major faces of said leading-out wiring board, and the lower face electrode of said piezoelectric element of said central portion being electrically led out by a lower one of said major faces of said leading-out wiring board.

2. An ultrasonic probe according to claim 1, wherein said leading-out wiring board is interposed between said piezoelectric elements of said one end and central portions and said backing member.

3. An ultrasonic probe according to claim 1, wherein said electrically conducting path on said lower face is extended to the upper face of said leading-out wiring board via a through-hole at a tip end of said leading-out wiring board.

4. An ultrasonic probe according to claim 3, wherein said leading-out wiring board comprises a flexible printed board.

5. An ultrasonic probe according to claim 2, wherein a cutting aperture for separating between said piezoelectric elements of said one end and central portions reaches said leading-out wiring board.

6. An ultrasonic probe according to claim 1, wherein said ultrasonic probe comprises a plurality of said piezoelectric elements.

7. An ultrasonic probe according to claim 1, further comprising a second leading-out wiring board having an electrical conductive path on only an upper face thereof, wherein a lower electrode of said piezoelectric element of the other end portion is lead out by said second leading-out wiring board.

8. An ultrasonic probe according to claim 7, wherein said second leading-out wiring board is interposed between said piezoelectric element of said other end portion and said backing member.

9. An ultrasonic probe according to claim 3, further comprising a second leading-out wiring board constituted by a flexible printed board and having an electrical conductive path on only an upper face thereof, wherein a lower electrode of said piezoelectric element of the other end portion is lead out by said second leading-out wiring board.

10. An ultrasonic probe according to claim 9, wherein said second leading-out wiring board is interposed between said piezoelectric element of said other end portion and said backing member.

* * * * *